United States Patent [19]

Genese

[11] 4,041,934
[45] Aug. 16, 1977

[54] ARTERIAL BLOOD SAMPLING UNIT

[75] Inventor: Joseph Nicholas Genese, Waukegan, Ill.

[73] Assignee: Abbott Laboratories, North Chicago, Ill.

[21] Appl. No.: 654,680

[22] Filed: Feb. 2, 1976

[51] Int. Cl.² ............................................. A61B 5/14
[52] U.S. Cl. ............................ 128/2 F; 128/DIG. 5
[58] Field of Search ............ 128/2F, 220, 221, 218 P, 128/218 M, 218 D, 218 DA, 272, 276, DIG. 5

[56] References Cited
U.S. PATENT DOCUMENTS

| 3,304,934 | 2/1967 | Bautista | 128/2 F |
| 3,378,008 | 4/1968 | Ogle | 128/220 |
| 3,645,252 | 2/1972 | Gilford | 128/2 F |
| 3,753,432 | 8/1973 | Guerra | 128/2F |
| 3,886,930 | 6/1975 | Ryan | 128/2 F |
| 3,890,956 | 6/1975 | Moorehead | 128/2 F |
| 3,930,492 | 1/1976 | Hatsuno et al. | 128/2 F |

Primary Examiner—John D. Yasko
Attorney, Agent, or Firm—Robert L. Niblack; Neil E. Hamilton

[57] ABSTRACT

An arterial blood sampling unit which is preassembled in a unitary device and which contains a sealing and stopper piercing element which is movable in a barrel member under the influence of arterial blood pressure so as to permit blood to be automatically collected in the syringe barrel. Preferably the unit is preloaded with an anticoagulant material so that upon the depression of a plunger member, the blood collecting chamber and the needle will be pretreated with an anticoagulant. After discarding the excess anticoagulant and upon injection of a hypodermic needle into an artery, the vial will automatically fill with blood without manipulation on the part of the operator.

17 Claims, 13 Drawing Figures

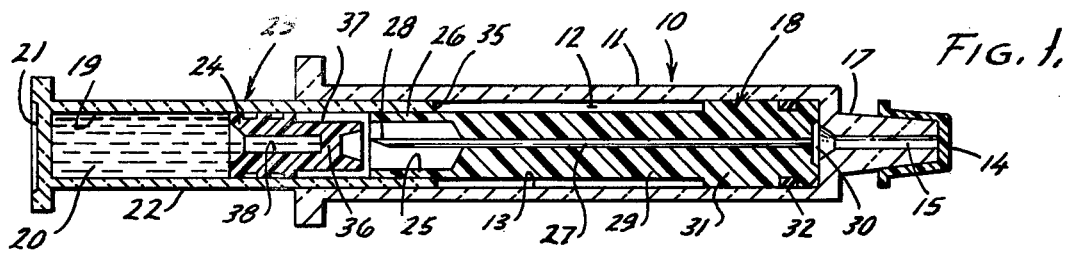
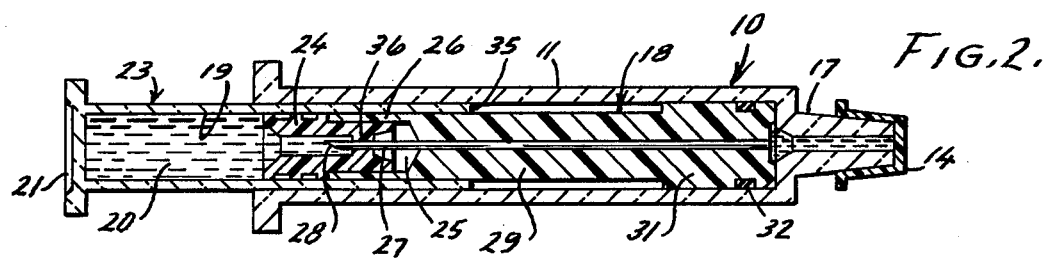
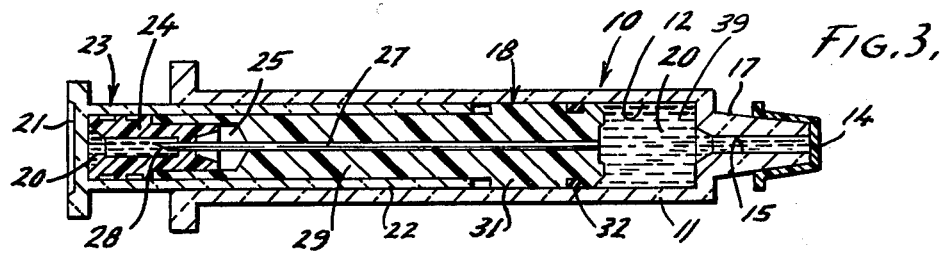
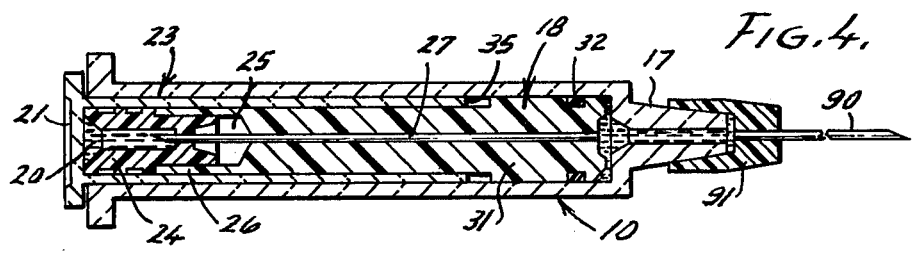
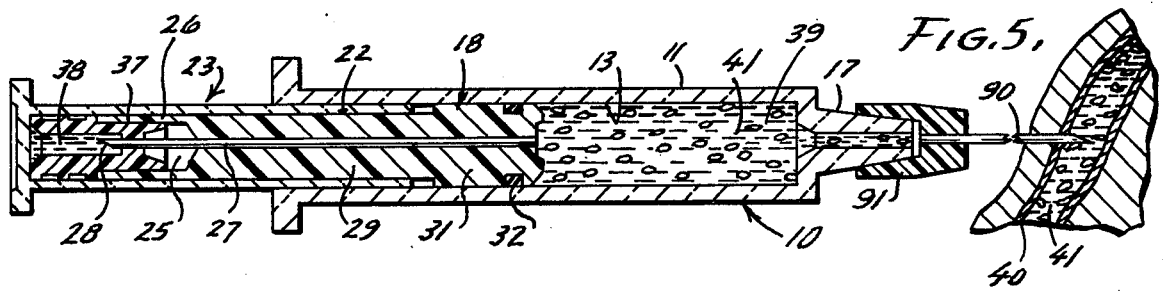

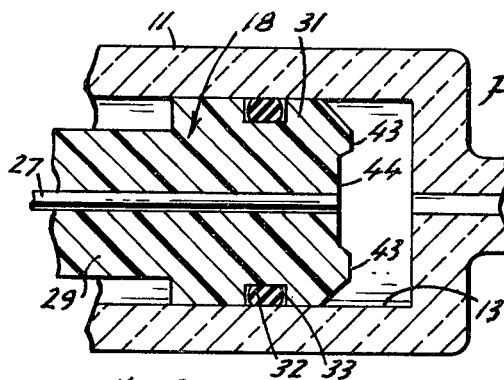
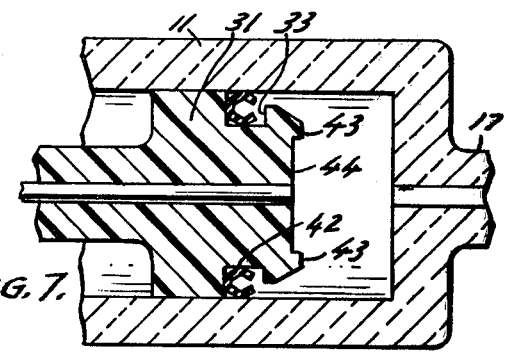
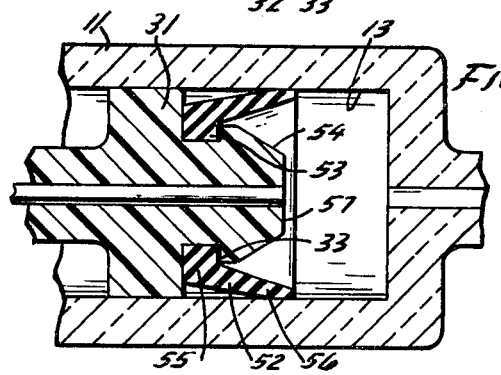
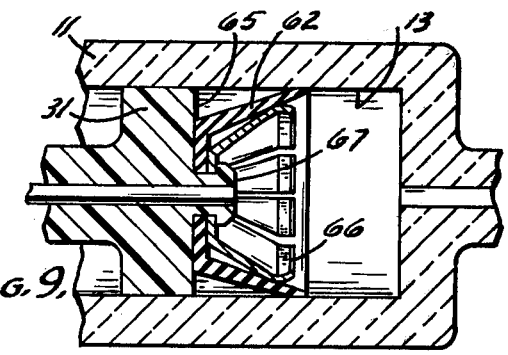
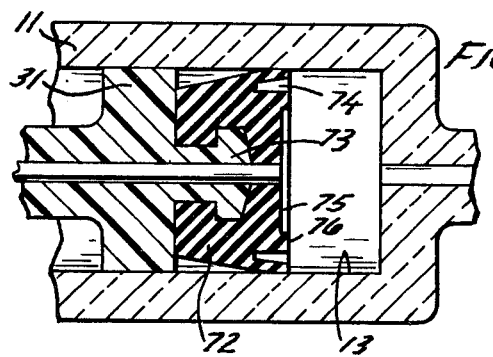
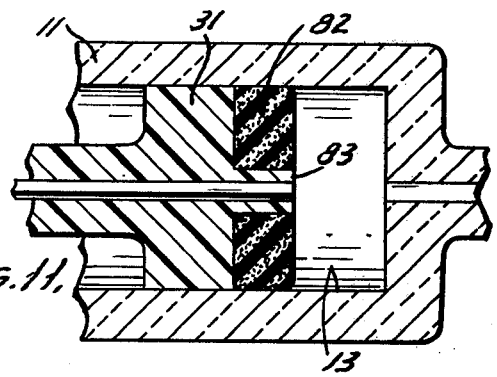
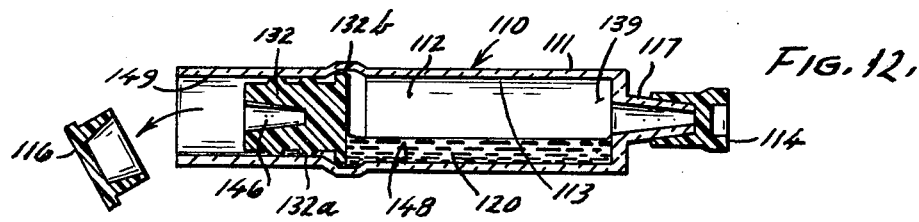
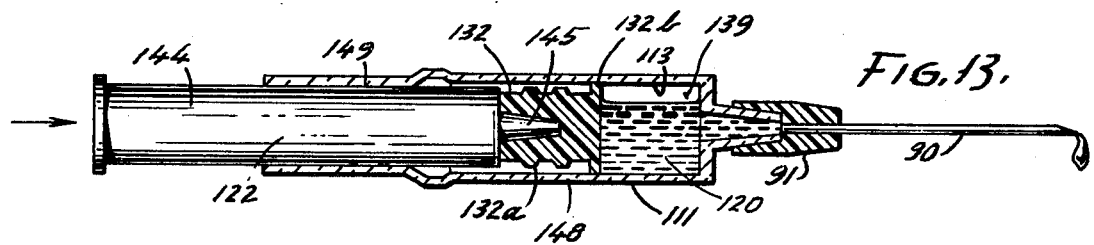

4,041,934

ARTERIAL BLOOD SAMPLING UNIT

BACKGROUND OF THE INVENTION

This invention relates to a blood sampling unit which will permit its utilization without the preassembly of parts. More particularly, it relates to an arterial blood sampling device with a sealing and stopper piercing element which will allow arterial blood pressure to move it along the inside of a syringe barrel and permit blood to collect in a sealed chamber created thereby. The invention also relates to an arterial blood sampling unit which contains an anticoagulant which is activated into the sampling unit prior to its use.

Blood sampling is commonly effected by the utilization of an evacuated container and in conjunction with a piercing apparatus such as described in U.S. Pat. No. 3,886,930. A syringe-type unit for blood collection is described in U.S. Pat. No. 3,753,423. The utilization of a syringe with a preassembled vial is taught in U.S. Pat. No. 3,378,008. As indicated, all of the prior art devices either utilize an evacuated container or the manipulation of a syringe in order to effect a vacuum so as to collect blood into a syringe chamber or vial. In those instances where an evacuated container or a syringe is utilized, it must first be treated with an anticoagulant so that blood clots do not occur when the blood is being collected.

Nowhere in the prior art is there available a blood sampling unit which is preassembled in such a manner that the operator does not have to preassemble components of the unit nor that precautions must be taken to assure that a vacuum is contained in a container prior to its use. Neither is there available a preassembled unit which contains an anticoagulant wherein the device can be easily treated with an anticoagulant material nor a unit which is self-actuating in that the arterial blood will actuate a sealing element so as to fill a container or vial without the presence of air.

It is an advantage of the present invention to afford a novel blood sampling unit which is preassembled and can be activated with a minimum number of manipulative steps. Other advantages are a blood sampling unit which contains an anticoagulant material and a combined stopper and sealing element which is actuated by blood pressure so as to afford a chamber in the blood collecting container, a blood sampling unit which obviates an evacuated container yet does not require the manipulation of a syringe plunger to withdraw blood from a blood vessel, a blood sampling unit which is easy to manufacture and assemble as well as a unit which is fabricated in such a way that it is disposable.

SUMMARY OF THE INVENTION

The foregoing advantages are accomplished and the shortcomings of the prior art are overcome by the present blood sampling unit which has a barrel member wherein there is positioned a low-friction-type sealing element which is activated by arterial blood pressure so as to move in the barrel or tubular member as pressure is exerted on it and thereby provide a chamber for the arterial blood. An anticoagulant material is contained in the tubular member so as to treat it prior to use and which can be expelled from the chamber by means of movement of the sealing element. In one embodiment, the sealing element carries a tubular member having a piercing tube which will pierce a stoppered vial of anticoagulant and upon movement of the vial inwardly over the slidable tubular member will effect the flow of anticoagulant material between the sealing element and the nozzle end of the syringe. Upon further movement the anticoagulant material will be expelled from the unit. Upon insertion into an artery, blood under normal pressure will then flow back into the syringe and contact the sealing element thereby moving it away from the nozzle end and also will carry with it the vial previously containing the anticoagulant material.

In an alternative embodiment, anticoagulant material is sealed in a syringe barrel between the nozzle and the low resistance sealing element. A needle adapter is attached and a plunger rod is then employed to move the sealing element in the direction of the nozzle and expel the anticoagulant material. The needle is inserted into an artery whereupon arterial blood will flow into the chamber and against the sealing element causing it to slidably move with the plunger in the barrel without manipulation by the operator and thereby fill the syringe barrel to the desired amount.

BRIEF DESCRIPTION OF THE DRAWING

A better understanding of the present unit will be afforded by reference to the drawing wherein:

FIG. 1 is a view in vertical section illustrating the preferred embodiment of the arterial blood sampling unit showing it in a preassembled condition with a vial containing an anticoagulant material.

FIG. 2 is a view similar to FIG. 1 except showing the sampling unit in the next step of operation with the piercing tube engaging the stopper in the vial with the anticoagulant.

FIG. 3 is a view similar to FIGS. 1 and 2 showing the next step of the operation with the anticoagulant material placed between the sealing member and the nozzle.

FIG. 4 is a view similar to the previous FIGURES showing the unit prior to its being inserted into an artery and with the anticoagulant expelled.

FIG. 5 is a view in vertical section showing the unit in fluid contact with an artery and illustrating the flow of arterial blood into the sampling device.

FIG. 6 is a partial enlarged view in vertical section illustrating the sealing element of the combined stopper piercing and slidable member utilized in the blood sampling units in FIGS. 1-5.

FIGS. 7-11 are views similar to FIG. 6 illustrating alternative embodiments of a sealing element for the combined stopper piercing and slidable member.

FIGS. 12 and 13 show an alternative embodiment of the blood sampling unit of this invention.

DESCRIPTION OF THE PREFERRED EMBODIMENT

Proceeding to a detailed description of the present invention, and particularly FIGS. 1-6, the blood sampling unit 10 is composed of a barrel member 11 having the usual tubular chamber 12 defined by an internal wall 13. A passage 15 is disposed at one end of the barrel member 11 through a nozzle member 17. Placed in sliding and sealing engagement inside tubular chamber 12 is a combined stopper piercing and low friction slidable member 18 which has a head portion 31 carrying an annular, low friction sealing element 32 as well as stop members 43 as best seen in FIG. 6. Extending from head portion 31 is a central shaft 29 containing a piercing tube 27 with a piercing end 28 which is housed in an annular compartment 25 defined by annular wall 26 secured to central shaft 29 and opposite to head 31.

Disposed a short distance over annular wall 26 is a tubular vial 23 containing a closure stopper 24 to form a chamber 19 for anticoagulant material 20 which is sealed therein by means of the stopper and the closed end 21 for vial 23. It will be noted that piercing tube 27 extends from annular compartment 25 into a small central compartment 30 in head 31. It is thereby placed in open communication with the inside of tubular chamber 12 as well as opening 15 in nozzle 17. A removable friction-type cap 14 is placed over nozzle 17, and when it is desired to utilize the blood sampling unit, a hypodermic needle 90 with a needle adapter 91 is placed thereon, as best shown in FIG. 4.

Referring to FIG. 6, it will be seen that sealing element 32 is of the annular type and is housed in a circumferential groove 33 in cylindrical head member 31 of the combined piercing and slidable member 18. As indicated in this instance, sealing member 32 is composed of an annular semi-rigid band formed from a rubber-like material and will be retained in groove 33 by means of its resilient nature. The head member 31 for the piercing and low friction slidable member 18 is substantially the same in the embodiments of FIGS. 7–11 as is the barrel member 11. Consequently, these elements are noted by the same numbers throughout. In FIG. 7 it will be seen that a C-shaped sealing element 42 is housed in cylindrical head 31 in a circumferential groove 33 instead of an annular sealing element 32 as in FIG. 6. This sealing material is preferably polytetrafluoroethylene. However, it can be fluorinated ethylene, propylene or other such polymeric material characterized by chemical inertness, low coefficient of friction, and nonstick properties. Sealing element 42 will be retained in groove 33 by means of a friction resilient fit.

In FIG. 8, head 31 is defined by a conical end 54 having a step-like portion 53 with groove 33 for housing an annular base portion 55 of the conical sealing element 52. A flexible wall 56 of sealing element 52 extends from groove 33 and contacts inner wall 13 of barrel 11 beyond end wall 57.

FIG. 9 illustrates a cup-shaped sealing element 62 and the annular groove 33 is eliminated. Cup-like sealing element 62 is seated on a head surface 65 by means of an inner radial projecting spring member 66 which is centrally disposed in sealing element 62 by means of deformed end of tubular protrusion 67. It will be noted as is true in the sealing element 52 in FIG. 8, that only a portion of the sealing element contacts the inner wall 13.

In FIG. 10, a frustoconical member 72 is provided and is retained on head 31 by means of a substantially T-shaped projection 73 extending from head 31 and accommodated in a like opening in the sealing element 72. Adjacent to the contact surface of the sealing element with the inner wall 13 is an annular compartment 74 which will aid in the flexibility of that portion of the sealing element contacting wall 13.

FIG. 11 shows an annular sealing element 82 which is seated on central projection 83 by means of an accommodating central opening in the sealing element and is disposed substantially over the entire end portion of head 31. In this instance the sealing element 82 is composed of closed cell, foamed, polymeric material similar to cis-1,4 polyisoprene or isobutylene-isoprene copolymer or polyurethane and is retained on head 31 and projection 83 by means of a suitable adhesive.

In FIGS. 12 and 13 an alternative embodiment 110 is described with similar parts being indicated with similar numbers with respect to unit 10 except in the "100" series. A syringe-like barrel member 111 has a nozzle 117 closed by removable cap 114 at one end and a second removable cap 116 at the other. A combined high and low friction sealing member 132 is disposed in barrel member 111 of tubular chamber 112 to form a chamber 119 for an anticoagulant material 120. It should be noted that sealing member 132 has a low resistance to friction portion 132b and a high resistance to friction portion 132a. This low and high resistance effect is accomplished by barrel being formed with a large diameter portion 148 and a small diameter portion 149. This permits high resistance to friction portion 132a to clear barrel portion 148. A solid rod 144 having a conical projection 145 engages sealing member 132 having an accommodating compartment 146 for this purpose to form a plunger member 122.

OPERATION

A better understanding of the advantages of blood sampling units 10 and 110 will be had by a description of their operation. Referring to sampling unit 10 first, the unit will be assembled and packaged for use as indicated in FIG. 1. Unit 10 will have an anticoagulant material 20, namely sodium heparin, sealed in vial 23 by means of pierceable stopper 24 and the closed end 21 of vial 23. As best seen in FIG. 1, the annular open end wall portion 35 of vial 23 will be seated over annular wall 26 of low friction slidable member 18. In this position, the piercing end 28 of piercing tube 27 will be spaced from the closed portion 36 of stopper 24. When it is desired to activate unit 10, vial 23 will be moved inwardly into barrel 11 in the usual manner of actuating a hypodermic syringe. This motion will cause the open end 35 of vial 23 to move inwardly into the barrel tubular chamber and also will cause the reduced diameter section 37 of stopper 24 to move into annular compartment 25 of combined piercing and slidable member 18 thereby causing a placement of the unit as shown in FIG. 2. In this position, the piercing 28 of piercing tube 27 is now positioned in an open central chamber 38 of stopper 24. This in effect will cause communication between vial 23 and closed nozzle 17. Continued movement of vial 23 into syringe barrel 11 and over annular wall 26 of slidable member 18 will move the closed end 21 of vial 23 in the direction of stopper 24 thereby forcing the anticoagulant in the direction of nozzle 17. The force of fluid in the chamber 39 adjacent nozzle 17 will cause the head portion 31 of low friction slidable member 18 to move away from nozzle portion 17 and at the same time stopper 24 will come to rest against closed end 21 with end 35 of vial 23 spaced from head 31. This is seen in FIG. 3. It should be noted that flow of anticoagulant material between head 31 and nozzle 17 will be aided by projection 43 spacing head 31 from nozzle 17 to form compartment 44.

At this stage, cap 14 will be removed and needle 90 with adapter 91 will be placed on nozzle 17. Further movement of vial 23 into syringe barrel 11 will cause an ejection of the anticoagulant through needle 90 and will then in effect treat the entire system with the anticoagulant material. The unit, as shown in FIG. 4, is now ready for injection into an artery as indicated by the numeral 40. When proper injection is made, blood as indicated by 41 will flow into syringe barrel 11 as indicated in FIG. 5. The slidable member 18 due to the low friction annular sealing element 32 will slide along the wall 13 of syringe with a very low amount of friction and under the influence of arterial blood pressure. As stopper 24 in vial 23 is locked onto the low friction slidable member 18 by means of annular wall 26 engaging reduced diameter section 37 of stopper 24, the vial 23 will be carried automatically outwardly from the syringe under the influence of the arterial blood pressure and without any manipulation on the part of the operator.

The arterial blood unit 110 shown in FIGS. 12 and 13 is similar in its operation as that of unit 10. Instead of a preloaded vial 23, this particular unit has the anticoagulant 120 sealed in the chamber 139 by means of sealing member 132. When it is desired to utilize this unit, cap 116 will be removed and sealing member 132 will be engaged by solid rod 144 engaging sealing member 132 by means of conical projection 145 and conical compartment 146. The anticoagulant – heparin material 120 will be removed from the syringe by the forward motion of rod 144 which will expel the anticoagulant material through needle 90. The collection of the blood will be as previously described in unit 10 with the blood being collected in chamber 139 as it flows into the syringe barrel and the pressure of which will move stopper 132 automatically outwardly as only low friction portion 132b will be in contact with barrel wall 113 and specifically large diameter portion 148 while small diameter portion 132a is not. Rod 144 will be carried with stopper 132 until high resistance to friction portion 132a engages small diameter portion 149 of barrel 111.

In the foregoing description, sealing elements 32, 42, 52, 62, 72, 82 and sealing portion 132b are stated as being of a low-friction type. These are composed of materials such as very low durometer elastomeric materials possibly coated with a permanent coating of a fluorosilicone or fluorocarbon, or as in the case for sealing elements 42, 52, 62, solid fluorocarbons as have been previously described, which will have a coefficient of friction of about 0.04 maximum. To further reduce the frictional resistance, internal wall 13 could be coated with a bonded-on coating of a silicone-based lubricant and the seal would be lightly coated with a silicone oil at time of assembly. In this manner the sealing elements and the barrel wall section engaged by the sealing elements cooperate to form a low friction sealing element.

It will thus be seen that through the present invention there is now provided a blood sampling unit which can be packaged for immediate use and requires a minimum number of manipulative steps by the operator. The unit contains a low friction sealing element which will automatically fill with arterial blood without withdrawal of a syringe plunger rod or by use of a vacuumized container. The unit can be fabricated from standard materials with various types of sealing elements available as alternative choices.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:
1. A blood sampling unit comprising:
   a barrel member defining a substantially tubular chamber having an internal wall section,
   means defining a nozzle member communicating with said tubular chamber for attachment with a cap member in one instance and a needle in another instance,
   a slidable member including a passage means in open communication with opposing ends of said slidable member, said slidable member having a closure piercing portion communicating with said passage means,
   a sealing element operatively associated with said slidable member and disposed opposite said closure piercing portion, said sealing element constructed and arranged to engage the internal wall section of said barrel member,
   said sealing element and said internal wall section engaged by said sealing element cooperating to provide a low friction sealing element,
   said sealing element composed of a material having a coefficient of friction sufficient to permit said slidable member to be moved in said tubular chamber under the influence of arterial blood pressure,
   a stoppered vial containing an anticoagulant material constructed and arranged to be accommodated within said tubular chamber of said barrel and engaged by said slidable member so that upon movement of said vial into said barrel said piercing portion of said slidable member will penetrate through said stopper of said vial and effect flow of anticoagulant material through said passage member and by means of further movement of said vial will effect placement of said anticoagulant material between said low friction sealing element and said nozzle member.

2. The blood sampling unit as defined in claim 1 wherein said slidable member includes a central shaft member and said passage means is defined by a tubular member housed therein with said piercing portion defined by a piercing end of said tubular member.

3. The blood sampling unit as defined in claim 2 wherein said central shaft member terminates at one end in a central compartment and said piercing end of said tubular member is disposed in said compartment.

4. The blood sampling unit as defined in claim 3 wherein said vial is sealed by a closure having a reduced diameter section which is constructed and arranged to fit with the compartment of said central shaft member.

5. The blood sampling unit as defined in claim 1 wherein said low friction sealing element is defined by a substantially cylindrical head member having a circumferential groove with a solid annular semirigid sealing member therein.

6. The blood sampling unit as defined in claim 1 wherein said low friction sealing element is defined by a substantially cylindrical head member having a circumferential groove with a substantially C-shaped, semirigid sealing member therein.

7. The blood sampling unit as defined in claim 1 wherein said low friction sealing element is defined by a cylindrical head member having a step-like portion with a conical sealing member attached thereto.

8. The blood sampling unit as defined in claim 1 wherein said low friction sealing element is defined by a substantially cylindrical head member and a cup-shaped seal carried thereby and an inner spring secured to said head biasing the edges of said cup-shaped seal against the internal wall section of said barrel member.

9. The blood sampling unit as defined in claim 1 wherein said low friction sealing element is defined by a substantially cylindrical head member with a frustoconical sealing member attached thereto and having a portion of the outer wall surface in contact with the internal wall section of said barrel member with an annular portion of the sealing member removed adjacent the contact surface of said sealing member.

10. The blood sampling unit as defined in claim 1 wherein said low friction sealing element is defined by a substantially cylindrical head member with a sealing member attached thereto and being of an annular configuration and disposed substantially over the end portion of said head member.

11. The blood sampling unit as defined in claim 1 wherein said anticoagulant material is disposed in said barrel and is composed of heparin.

12. The blood sampling unit as defined in claim 1 wherein said means defining a low friction sealing portion has a coefficient of friction less than about 0.04.

13. The blood sampling unit as defined in claim 1 further including a lubricant material coated on the internal wall of said barrel member engaged by said low friction sealing element.

14. The blood sampling unit as defined in claim 12 wherein said sealing element is coated with a lubricant material.

15. A blood sampling unit comprising:
a barrel member defining a substantially tubular chamber having an internal wall section, said barrel member formed with a small and a large diameter portion,
means defining a nozzle member communicating with said tubular chamber, said nozzle member adapted to receive means to close said tubular chamber to the outside atmosphere as well as to receive a needle,
a sealing element formed with a low and a high friction sealing portion with said low friction portion adapted to contact said large diameter portion and said high friction sealing portion adapted to contact said small diameter portion,
said sealing element when contacting said small diameter portion of said barrel member by means of said high friction sealing portion providing a chamber for an anticoagulant material in said large diameter portion,
said small diameter portion being of sufficient dimension to receive a plunger member which cooperates with said sealing element to move said high friction sealing portion into said large diameter portion, said low friction sealing portion cooperating with said large diameter portion of said barrel to provide a coefficient of friction sufficient to permit the sealing element and the plunger member to be moved in said large diameter portion under the influence of arterial blood pressure.

16. The blood sampling unit as defined in claim 15 further including removable cap members enclosing said barrel member and said nozzle member with said anticoagulant material occupying a portion of said barrel between said high friction sealing portion and said nozzle member.

17. The blood sampling unit as defined in claim 16 further including a solid rod member with means to engage said low friction sealing element and forming a plunger.

* * * * *